US006194546B1

(12) United States Patent
Newton et al.

(10) Patent No.: US 6,194,546 B1
(45) Date of Patent: Feb. 27, 2001

(54) FUSION PROTEINS

(75) Inventors: Susan Elizabeth Newton, Victoria (AU); Berwyn Ewart Clarke, Beckenham (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/841,650

(22) Filed: Apr. 30, 1997

Related U.S. Application Data

(63) Continuation of application No. 08/471,266, filed on Jun. 6, 1995, now Pat. No. 5,700,680, which is a continuation of application No. 08/116,557, filed on Sep. 7, 1993, now abandoned, which is a continuation of application No. 07/856,806, filed on Mar. 24, 1992, now abandoned, which is a continuation of application No. 07/545,766, filed on Jun. 28, 1990, now abandoned, which is a continuation of application No. 07/012,943, filed on Feb. 10, 1987, now abandoned.

(51) Int. Cl.$^7$ .......................... C07K 14/11; C07K 14/445

(52) U.S. Cl. ............................................ 530/350; 530/395

(58) Field of Search .................................. 424/93.2, 93.6, 424/185.1, 186.1, 199.1, 192.1, 209.1, 210.1; 530/350, 395; 514/2, 44

(56) References Cited

U.S. PATENT DOCUMENTS

| 4,659,669 | 4/1987 | Kleid et al. ...................... 435/252.33 |
| 4,710,463 | 12/1987 | Murray ................................ 435/69.3 |
| 4,722,840 | 2/1988 | Valenzuela et al. ............... 424/192.1 |

FOREIGN PATENT DOCUMENTS

| 0 013 828 A1 | 8/1980 | (EP) . |
| 0 083 286 | 7/1983 | (EP) . |
| 0 175 261 | 3/1986 | (EP) . |
| 0 176 493 | 4/1986 | (EP) . |
| 0 182 442 A2 | 5/1986 | (EP) . |
| 0 492 920 A1 | 7/1992 | (EP) . |
| 2103662 | 2/1983 | (GB) . |
| 830 2393 | 7/1983 | (WO) . |

OTHER PUBLICATIONS

Rabinovich et al., Science, vol. 265, pp.1401–1404, Sep. 2, 1994.*
Cohen, Jon, Science, vol. 265, pp. 1371–1373, Sep. 2, 1994.*
Oldstone, M. B. A., Virology, vol. 234, pp. 179–185, 1997.*
Verhoeyen et al "Antigenic Drift Between the Haemagglutinin of the Hong Kong Influenza Strains A/Aichi/Feb. 1968 and A/Victoria/Mar. 1975"Nature, 286, 771–776, 1980.
Gething et al "Cloning and DNA Sequence of Double–Stranded Copies of Haemagglutinin Genes From H2 and H3 Strains Eluridates Antigenic Shift and Drift in Human Influenza Virus" Nature, 287, 301–306, 1980.

Wilson et al "Structure of the Haemagglutinin Membrane Glycoprotein of Influenza Virus at 3Å Resolution" Nature, 289, 366–373, 1981.
Wiley et al "Structural Identification of the Antibody–Binding Sites of Hong Kong Influenza Haemagglutinin and Their Envolvement in Antigenic Variation" Nature, 289, 373–378, 1981.
Heiland and Gething "Cloned Copy of the Haemagglutinin Gene Codes for Human Influenza Antigenic Determinants in *E. coli*" Nature, 292, 851–852, 1981.
Gething and Sambrook "Cell–Surface Expression of Influenza Haemagglutinin From a Cloned DNA Copy of the RNA Gene" Nature, 293, 620–625, 1981.
Gething and Sambrook "Construction of Influenza Haemagglutinin Genes That Code for Intracellular and Secreted Forms of the Protein" Nature, 300, 598–603, 1982.
Smith et al "Construction and Characterisation of an Infectious Vaccina Virus Recombinant That Expresses the Influenza Hemagglutinin Gene and Induces Resistance to Influenza Virus Infection in Hamsters" Proc. Natl. Acad. Sci. USA, 80, 7155–7159, 1983.
Morein et al "Iscom, a Novel Structure for Antigenic Presentation of Membrane Proteins From Enveloped Viruses" Nature, 308, 457–460, 1984.
Brown et al "Recombinant Vaccinia Viruses as Vaccines" Nature, 319, 549–550, Feb. 13, 1986.
Winther et al "Bacterially Expressed Antigenic Peptide From Foot–and–Mouth Disease Virus Capsid Elicits Variable Immunologic Responses in Animals" J. Immunol. 136, 1835–40, 1986.
Newton et al "Expression of a Foot–and–Mouth Disease Virus Immunogenic Site Sequence in Vaccinia Virus" Vaccines 86, Cold Spring Harbor Laboratory, 303–309, 1986.
Broekhuijsen et al "Synthesis of Fusion Proteins Containing Antigenic Determinants of Foot–and–Mouth Disease Virus" Vaccine, 4, 119–124, 1986.
Newton et al. "New Approaches to FMDV Antigen Presentation Using Vaccinia Virus" Presented on Sep. 9, 1986 and Appearing in Vaccines 87, Cold Spring Harbor Laboratory, 12–21, 1987.
Newton et al "Expression of Foot–and–Mouth Disease Virus Immunogenic Site Sequences on Fusion Proteins Using Vaccinia Virus" The Vaccines Meeting, Lorne, Australia, Oct. 1986.
Riechman, et al, "Reshaping Human Antibodies for Therapy", *Nature,* vol. 332, Mar. 24, 1988, pp. 323–327.

(List continued on next page.)

Primary Examiner—David Guzo
(74) Attorney, Agent, or Firm—Nixon & Vanderhye P.C.

(57) ABSTRACT

A DNA sequence encoding a fusion protein comprising influenza virus HA, at a site of which normally occupied by a natural antigenic epitope thereof a different antigenic epitope is provided, is incorporated in a vector which is capable of expressing the fusion protein when provided in a eucaryotic host. When in the form of a viral vector such as a recombinant vaccinia virus, the vector can be used as a vaccine. Alternatively, the fusion protein expressed by the host can be recovered and provided as a vaccine.

4 Claims, 4 Drawing Sheets

OTHER PUBLICATIONS

Doms, et al, Minireview: "Folding and Assembly of Viral Membrane Proteins", pp. 545–562, 1993.

Jaenicke, "Folding and Association of Proteins", *Prog. Biophys. molec. Biol.,* vol. 49, pp. 117–237, 1987.

Bialy, "Recombinant Proteins: Virtual Authenticity", *Biotechnology,* vol. 5, No. 9, Sep. 1987, pp. 883–890.

Copeland, et al., "Assembly of Influenza Hemagglutinin Trimers and Its Role in Intracellular Transport", *The Journal of Cell Biology,* vol. 103, Oct. 1986, pp. 1179–1191.

Gething, et al., "Expression of Wild–Type and Mutant Forms of Influenza Hemagglutinin: The Role of Folding in Intracellular Transport", *Cell,* vol. 46, Sep. 12, 1986, pp. 939–950.

Gallione, et al, "A Single Amino Acid Substitution in a Hydrophobic Domain Causes Temperature–Sensitive Cell–Surface Transport of a Mutant Viral Glycoprotein", *Journal of Virology,* vol. 54, No. 2, May 1985, pp. 374–382.

Wu, et al, Secretion of a $\lambda_2$ Immunoglobulin Chain is Prevented by a Single Amino Acid Substitution in Its Variable Region, *Cell,* vol. 33, May 1983, pp. 77–83.

King, "Genetic Analysis of Protein Folding Pathways", *Biotechnology,* vol. 4, Apr. 1986, pp. 297–303.

Jones, et al, "Replacing the Complementarity–Determining Regions in a Human Antibody with those from a Mouse", *Nature,* vol. 321, May 29, 1986, pp. 522–525.

Cohen, et al, "Electron Microscopy of Hepatitis B Core Antigen Synthesized in *E. coli*", *Nature,* vol. 296, Apr. 15, 1982, pp. 677–678.

Murray, et al, "Hepatitis B Virus Antigens Made in Microbial Cells Immunise Against Viral Infection", *The EMBO Journal,* vol. 3, No. 3, 1984, pp. 645–650.

Pasek, et al "Hepatitis B Virus Genes and Their Expression in *E. coli*", *Nature,* vol. 282, Dec. 6, 1979, pp. 575–579.

Stahl, et al "Differential Antibody Screening of Cloned *Plasmodium falciparum* Sequences Expressed in *Escherichia coli*: Procedure for Isolation of Defined Antigens and Analysis of Human Antisera", *Proc. Natl. Acad. Sci.,* vol. 81, Apr. 1984, pp. 2456–2460.

Stahl, et al, "Hepatitis B Virus Core Antigen: Synthesis in *Escherichia coli* and Application in Diagnosis", *Proc. Natl. Acad. Sci.,* vol. 79, Mar. 1982, pp. 1606–1610.

Burrell, et al, "Expression in *Escherichia coli* of Hepatitis B Virus DNA Sequence Cloned in Plasmid pBR322", *Nature,* vol. 279, May 3, 1979, pp. 43–47.

Robinson, "The Genome of Hepatitis B Virus", *Ann. Rev. Microbiol..* 1977, pp. 357–377.

McQueen et al, Polarized Expression of a Chimeric Protein in Which the Transmembrane and Cytoplasmic Domains of the Influenza Virus Hemagglutinin Have Been Replaced by Those of the Vesicular Stomatitis Virus G Protein, Proc. Natl. Acad. Sci. 83:9318 (1986).

Pouwels et al, Cloning Vectors (1985) VI–A–il, VI–I, VII–I–A–a–il.

* cited by examiner

Fig.3.

```
HindIII ─────────────────────────── AvaII ─ AccI
                                           HincII
            │
            │ +AvaII
            ▼
HindIII ─────────────────────────── AvaII         Site A removed │
            │ Ligate an annealed
            │ synthetic oliyonucleotides
            │ containing FMDV sequences,
            │ with AvaII-AccI
            │ overhangs
            ▼
HindIII ─────────────────────────── AvaII ─ AccI
                                    └──┬──┘
                                    FMDV sequences
                                    instead of site A
```

Ligate to HindIII-AccI cut mpsite A mp site A (circular):
- HindIII
- AvaII
- AccI
- HincII
- FMDV VPI sequences
- M13 sequencing primer Reclone altered HindIII-HincII fragment into pvHAΔH pvHA* (circular, PUC9):
- ClaI
- ΔHindIII
- TK
- pIIK
- PstI
- HindIII
- HincII
- HA
- FMDV VPI sequences
- HA
- PstI
- TK

Fig.4.

| Plasmid | Sequence at site A |
|---|---|
| pvHAX31 | C K R [G(142) P G S G(146)] F(147) F S  (141) |
| pvHA-80/81 | C K R [G(142) P | G(146) D L Q V L(151)] F(147) F S — FMDV VP1 |
| pvHA-82/83 | C K R [G(142)] [P(142) N L R(145)] F(147) F S — FMDV VP1 |
| pvHA-122/124 | C K R [G(142)] [P(142) N L R G D L Q V L(151)] [G(146)] F(147) F S — FMDV VP1 |

FUSION PROTEINS

This is a Continuation of application U.S. Ser. No. 08/471,266, filed Jun. 6, 1995, now U.S. Pat. No. 5,700,680; which is a continuation of U.S. Ser. No. 08/116,557, filed Sep. 7, 1993, now abandoned; which is a continuation of U.S. Ser. No. 07/856,806, filed Mar. 24, 1992, now abandoned; which is a continuation of U.S. Ser. No. 07/545,766, filed Jun. 28, 1990, now abandoned; which is a continuation of U.S. Ser. No. 07/012,943, filed Feb. 10, 1987, now abandoned.

This invention relates to the construction of fusion proteins.

In previous attempts to express immunogenic epitopes of foot-and-mouth disease virus (FMDV) using vaccinia virus protein, fusions have been made to beta-galactosidase. High levels of fusion protein were synthesised. However, animals vaccinated with the recombinant vaccinia virus failed to produce neutralizing antibody (Newton et al, 1986). The reason for this poor response may be because beta-galactosidase is expressed in the cytoplasm. We have therefore investigated whether an antigen which is expressed on the surface of a cell would elicit a better response.

DNA sequences were constructed, each encoding a fusion protein comprising influenza virus haemagglutinin protein (HA) and, at antigenic site A of the HA, an epitope from part of the major FMDV antigenic site. The DNA sequences were incorporated into the vaccinia virus genome. Cells infected with the recombinant viruses not only expressed the fusion protein but did so such that the FMDV epitopes could be detected using anti-FMDV serum. Further, the infected cells reacted with polyclonal anti-HA antibody. It is therefore possible to change the sequence of influenza HA yet still retain all its properties of membrane insertion.

This approach for presenting antigenic epitopes to the immune system has general applicability. Accordingly, the present invention provides a DNA sequence encoding a fusion protein comprising influenza virus HA at a site of which normally occupied by a natural antigenic epitope thereof a different antigenic epitope is provided. In other words all or part of a natural antigenic epitope of HA may be replaced by a different antigenic epitope.

For expression of the fusion protein, the DNA sequence is incorporated in an expression vector. The DNA sequence is incorporated in a vector such that the vector, when provided in a eucaryotic host, is capable of expressing the fusion protein. A eucaryotic host is required for correct glycosylation of the HA. The vector may be a viral vector which incorporates the DNA sequence such that the fusion protein is expressed in cells infected with the vector. A vaccine may comprise such a viral vector and a physiologically acceptable carrier or diluent. In such an instance, the viral vector preferably is a recombinant vaccinia virus which incorporates the DNA sequence. Alternatively, a vaccine may comprise the fusion protein and a physiologically acceptable carrier or diluent.

Influenza virus HA is the most thoroughly studied integral membrane protein with detailed information available on its three-dimensional structure (Wilson et al, 1981) and its antigenicity (Wiley et al, 1981). The HA genes from several influenza subtypes have been expressed in a number of eukaryotic cells using various specific vectors (eg Smith et al, 1983; Gething and Sambrook, 1982). When expressed in recombinant vaccinia virus infected cells the HA is glycosylated normally and transported to the cell surface where it can be detected by serological methods.

Antigenic site A "loops out" from the surface of HA. This site can be determined by epitope mapping. Typically, it corresponds to HA amino acid residues 140 to 146. The HA may correspond to any influenza virus type or subtype. Consequently, it is at HA antigenic site A for example at which the antigenic epitope for the fusion protein is provided. All or part of site A may be replaced by the antigenic epitope. Typically, though, the epitope is inserted between HA residues 142 or 143 and residue 146 with the loss of the intervening HA residues. However, the antigenic epitope may be provided at any of the other natural antigenic epitopes of HA, sites B, C, D or E.

Any antigenic epitope may be provided at the natural antigenic epitope of HA. The epitope may be a corresponding epitope from a different type or subtype of influenza virus as that to which the HA corresponds. Alternatively or additionally, one or more of the other natural antigenic epitopes of HA of the same or of a different type or subtype of influenza virus may be provided. In this way a polyvalent influenza vaccine may be formed.

More usually, however, a heterologous antigenic epitope is provided. By "heterologous" is meant an epitope which is not an epitope of an influenza virus. The size of the heterologous epitope usually is larger than the portion of the HA site A which it replaces. The heterologous epitope may form part of a longer amino acid sequence. The insert may have from 4 to 26 amino acid residues. A heterologous antigenic epitope may be provided with an influenza virus epitope. Two or more heterologous antigenic epitopes may be provided. In this way, polyvalent vaccines can be presented.

The heterologous epitope may be that of a virus, bacterium or protozoan. As examples of viral epitopes, there may be mentioned those of FMDV, poliovirus human rhinovirus and hepatitis B virus. Protozoan whose epitopes may be provided include the malaria parasite *Plasmodium falciparum*.

The major FMDV antigenic sites correspond to amino acid residues 141 to 160 and 200 to 213 of the VP1 capsid protein. Either or both of these amino acid residues may therefore be provided, for example at site A. Alternatively parts of these sequences may be provided e.g. residues 142 to 145, 146 to 151 or 142 to 151. Suitable DNA constructs incorporating parts of the major antigenic site of FMDV type $O_1$ Kaufbeuren, and their corresponding amino acid sequences as denoted by the one-letter code, are shown below together with the DNA and amino acid sequences for HA.

```
                    140                                    150
     HA             AAA AGG GGA CCT GGT AGC GGT TTT TTC AGT AGA
                     K   R   G   P   G   S   G   F   F   S   R

HA-FMDV        AAA AGG GGA CCG AAC CTG CGT TTT TTC AGT AGA
     142-145         K   R   G   P   N   L   R   F   F   S   R
                              [142    FMDV    145]
```

```
                    -continued
HA-FMDV     AAA AGG GGA CCG GGT GAC CTG CAG GTT CTG TTT
146-151      K   R   G   P   G   D   L   Q   V   L   F
                        [146          FMDV        151]

TTC AGT AGA
             F   S   R

HA-FMDV     AAA AGG GGA CCG AAC CTG CGT GGT GAC CTG CAG
142-151      K   R   G   P   N   L   R   G   D   L   Q
                        [142          FMDV

GTT CGT GGT TTT TTC AGT
             V   L   G   F   F   S
                    151]
```

The DNA sequence encoding the fusion protein can be prepared by providing a DNA sequence encoding HA, for example as a plasmid, and modifying this sequence by providing in the correct frame at the site of the DNA encoding a natural antigenic epitope of HA a DNA sequence corresponding to the desired antigenic epitope it is wished to incorporate in the fusion protein. A vector capable of expressing the fusion protein may be prepared by incorporating the DNA sequence encoding the fusion protein between translational start and stop signals in a vector suitable for use in a eucaryotic host and providing a promoter for the sequence. By transforming eucaryotic host cells with such an expression vector, the fusion protein can be produced.

A viral vector for use as a vaccine may therefore be prepared by incorporating a DNA sequence encoding the fusion protein between translational start and stop signals in the genome of a virus and providing a promoter for the sequence. Typically, this may be achieved by:

(i) constructing a shuttle vector which incorporates, under the transcriptional control of a promoter, a DNA sequence encoding HA between translational start and stop signals;

(ii) modifying the DNA sequence by providing in the correct frame at the site of the DNA encoding a natural antigenic epitope of HA a DNA sequence corresponding to the antigenic epitope to be incorporated in the fusion protein; and (iii) transfecting with the shuttle vector and infecting with a virus mammalian cells such that the thus-modified DNA sequence and the promoter are incorporated in the viral genome.

The DNA sequence and the promotor are incorporated in the viral genome by homologous recombination. Appropriate flanking sequences of viral DNA are therefore provided on either side of the DNA sequence and promoter in the shuttle vector. The fusion protein is expressed by cells infected with the resultant recombinant virus.

The shuttle vector is typically a plasmid. It comprises a bacterial origin of replication to enable steps (i) and (ii) to be carried out in bacteria, especially *E. coli*. The promoter is typically a viral promoter, more preferably a promoter endogenous to the virus into the genome of which the DNA encoding the fusion protein is to be inserted. The antigenic epitope is generally prepared by chemical synthesis and/or by cloning. Some or all of the codons of the HA antigenic epitope may be excised from the shuttle vector prior to insertion of the DNA sequence encoding the epitope to be incorporated in the fusion protein.

A vaccinia virus system may be used. A shuttle vector may be constructed in which the HA gene is incorporated under the transcriptional control of a vaccinia promoter. A suitable promoter is the vaccinia p11k promoter. The promoter and HA gene are flanked by vaccinia virus DNA which is not essential for virus replication. Typically, flanking segments of the vaccinia gene for thymidine kinase (TK) are used. The HA gene is modified by insertion of DNA encoding the desired antigenic epitope to produce the fusion protein gene.

The vaccinia promoter and fusion protein gene are then inserted into the vaccinia genome by homologous recombination. This is typically achieved by infecting mammalian cells with vaccinia virus such as the Wyeth (US vaccine) strain and also transfecting the cells with the shuttle vector. The site of insertion is determined by the flanking vaccinia DNA segments of the shuttle vector. By means of homologous recombination the functional TK gene of the wild-type virus is replaced by the non-functional TK gene sequence included within which is the fusion protein gene. The resulting recombinant virus is TK$^-$ and can therefore be selected accordingly.

The fusion protein incorporating the antigenic epitope is expressed in cells infected with the recombinant viral vector. The fusion protein, it is believed, protrudes from the cell membrane in the manner of normal HA. This enables the antigenic epitope exposed on the surface of the HA to be recognized by the immune system and a suitable immune response mounted. The viral vectors may therefore be used as vaccines.

The fusion protein itself may alternatively be formulated in a vaccine. The fusion protein is produced by a host and recovered. Cells from vertebrates or invertebrates, preferably mammalian cells, can be used as host cell lines. Cell lines such as VERO, HeLa, CHO (Chinese hamster ovary), W138, BHK, COS-7, MDCK and CV-1 may be employed. Expression vectors for such cells generally contain an origin of replication, a promoter located in front of the gene to be expressed, and any necessary ribosome binding sites, RNA splice sites, polyadenylation site and trascriptional terminator sequences. Viral promoters preferably are employed. Viral vectors as above may be used, such as baculovirus expression system.

Eucaryotic microbes such as yeast cultures may alternatively be used as host cells. *Saccharomyces cerevisiae* strains can therefore be employed. A plasmid vector such as plasmid YRp7 is typically utilised to transform such hosts. Any plasmid vector containing a yeast-compatible promoter, origin of replication and termination sequences is suitable.

Vaccines may be administered in any appropriate fashion to a human or animal. The choice of whether an oral route or a parenteral route such as sub-cutaneous, intravenous or intramuscular administration is adopted depends upon the purpose of the vaccination and whether it is a human or mammal being vaccinated. Similar criteria govern the physiologically acceptable carrier or diluent employed in the vaccine preparation and the dose of vaccine.

Both the manner of formulation, the carrier or diluent and the dose for recombinant viral vaccines may be the conventional ones utilised when the unmodified virus is conventionally used as a vaccine. For example, recombinant vaccinia virus may be administered by the dermal route. A viral vector such as the recombinant vaccinia virus is typically administered, as regards all routes of administration, in an amount of 10–1000 μg per dose. More preferably from 10–100 μg of the virus is used. Fusion protein itself may be used as a vaccine in the form of an immunostimulating complex or "iscom" with the matrix of the iscom typically being the glycoside Quil A (Morein et al, 1984). Fusion protein may also be administered in an amount of 10–1000 μg per dose, more preferably 10–100 μg per dose, also as regards all routes of administration.

The following Example illustrates the invention. In the accompanying drawings:

BRIEF DESCRIPTION OF THE DRAWINGS

FIG. 3 shows the replacement of site A of the HA gene by a FMDVΔVP1 sequence; and FIG. 4 shows the FMDVΔVP1 sequences inserted in place of site A in the HA gene, amino acids being shown by the one-letter code.

EXAMPLE 1

Source of HA

Figure 1:
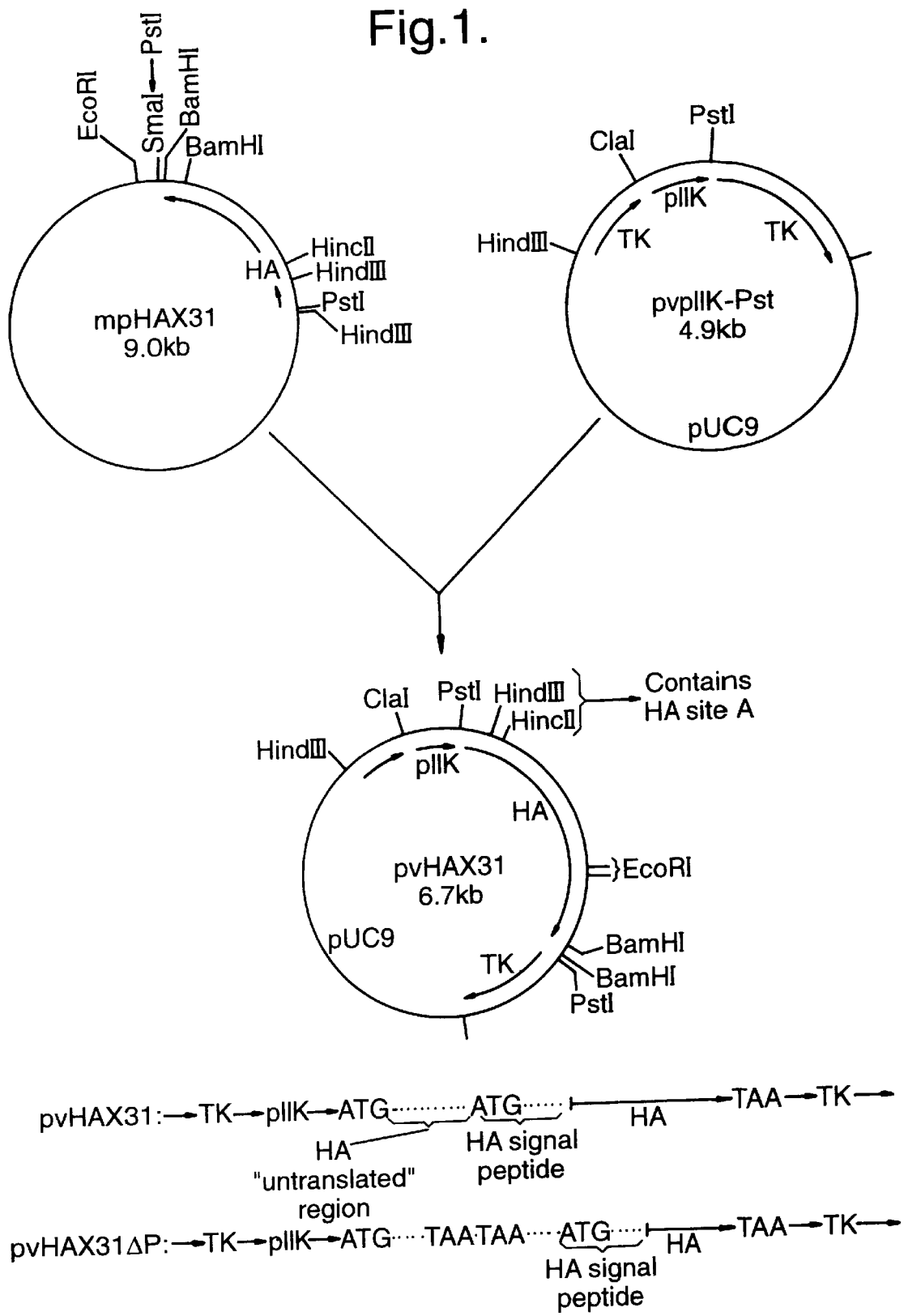
FIG. 1 shows the construction of plasmids pvHAX31 and pvHAX31ΔP.

A complete cDNA copy of the HA gene from influenza A/Aichi/2/68 (X31) (Verholyen et al, 1980) which had been cloned in M13 mp8 (Messing and Vieira, 1982) was obtained from Dr. John Skehel (NIMR, London) (see FIG. 1).

Expression of X31 HA using recombinant vaccinia viruses

In order to facilitate transfer of the HA gene to a vaccinia virus (VV) shuttle vector, the above plasmid was cut at the Sma I site within the mp8 polylinker, and a Pst I linker was inserted into this site, to form the clone mpHAX31. This enabled the complete HA gene to be isolated as a Pst I fragment.

The VV shuttle vector used was pvpIIk (see FIG. 1) which was derived from the vector pH3JΔRIA (Newton et al, 1986) by deletion of extraneous VV sequences. The shuttle vector has a VV promoter (in this case pIIk) inserted into the VV thymidine kinase (TK) gene. This vector has a unique Eco RI site immediately following the VV pIIk promoter and AUG (Berthelot et al, 1985). To adapt this vector for insertion of the HA gene, the plasmid was cut at the Eco RI site, the sticky-ends filled in using the Klenow fragment of DNA Polymerase I, and a Pst I linker inserted to form pvpIIk-Pst.

The HA gene was inserted as a Pst I fragment into Pst I-cut, dephosphorylated pvpIIk-Pst. Clones with the HA gene in the correct orientation relative to the pIIk promoter were identified by restriction mapping. This clone was designated pvHAX31 (see FIG. 1). In this construction, the natural HA AUG is in the same reading frame as the pIIk AUG. Therefore, since there are no in phase stop codons in the HA "untranslated" leader sequence, the expressed HA will be synthesised with an additional X amino acids at its N-terminus; these should be removed during transport and processing of the HA with the HA signal peptide.

In case the presence of the additional sequences was detrimental to maturation of the HA, a further construction was prepared. pvHAX31 was partially digested with Pst I and the sticky ends removed using T4 DNA polymerase (holoenzyme). The linear band was purified on an agarose gel, then re-ligated. Clones were screened for the removal of the correct Pst I site by restriction mapping. The correct clone was designated pvHAX31 P. This modification places stop codons in phase with the pIIk AUG, and should allow re-initiation at the authentic HA AUG (see FIG. 1).

Both these HA constructs were inserted into the genome of the Wyeth (US vaccine) strain of VV, under control of the VV pIIk promoter, by homologous recombination using the flanking TK sequence (Mackett et al, 1985 a and b). Individual progeny plaques with a TK$^-$ phenotype were tested for expression of HA by reacting methanol—or glutaraldehyde—fixed plaques in situ with rabbit polyclonal anti-HA serum, followed by goat anti-rabbit conjugated with horse radish peroxidase and colour development using 4-chlor-1-naphthol as substrate (Newton et al, 1986) (a "black plaque" assay). Purified plaques expressing HA+extra amino acids (vHAX31-J34c) or "natural" HA (vHAX31ΔP-K3) were grown up.

The level of expression of HA was similar in the two constructs (by rough estimation), so re-initiation in vHAX31 P was evidently efficient. Also, since the HA with extra N-terminal amino acids was expressed on the surface of cells infected with vHAX31, transport of this HA evidently unaffected by "junk" sequences at the N-terminus of the signal sequence.

Replacement of HA antigenic site A with FMDV sequences

In all experiments replacement of site A has been done using the pvHAX31 construct (i.e. with N-terminal "junk" amino acids). This plasmid was partially digested with HindIII and the sticky ends filled in as above. Linear plasmid was isolated and religated. Clones were screened for the removal of the HindIII site located at the 5' end of the VV TK gene; the correct clone was designated pvHAΔH. This clone now had a unique HindIII site located within the HAv gene 5' of site A.

Figure 2:
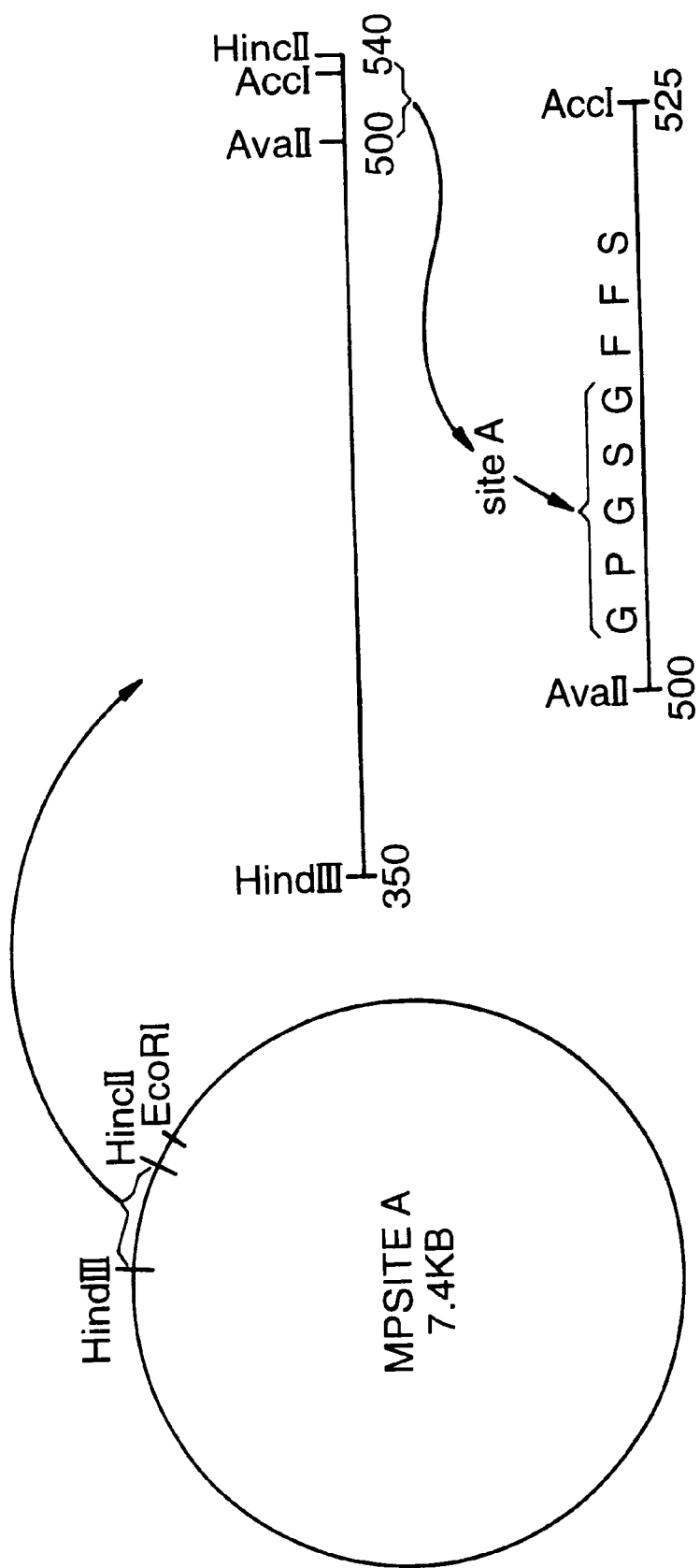
FIG. 2 shows the plasmid mpsite A, amino acids being shown by the one-letter code.

To facilitate manipulation of site A, pvHAΔH was cut off the unique HindIII and HincII sites, and the 180b fragment containing site A was subcloned into M13 mp11. The large fragment was also isolated for later use. Correct clones were identified by sequencing picked plaques; this clone was designated mpsite A (see FIG. 2). RF DNA from mpsiteA was cut with HindIII and AccI (the M13 polylinker AccI site was removed in the above construction, leaving only the HA AccI site at the 3' side of site A) and the 165 bp fragment purified on an agarose gel. The large fragment was also isolated for later use. This fragment was then cut with AvaII and the 145 bp HindIII-AvaII fragment purified on an acrylamide gel. This removes the HA site A sequences (FIG. 3).

Complementary synthetic oligonucleotides coding for FMDV sequences were prepared—these were constructed so that when annealed an AvaII overhang was left at the 5' end and an AccI overhang at the 3' end. These annealed oligonucleotides, the HA Hind III-AvaII fragment and the large HindIII-I fragment from mpsiteA were joined in a three-way ligation. Picked M13 plaques were sequenced to identify clones carrying FMDV sequences and to check the fidelity of the ologonucleotide synthesis and cloning, so as to ensure that the FMDV sequences were in the correct reading frame with the HA at both ends. RF DNA's from the various modified mpHA clones were cut with HindIII and HincII and the modified 180–200 bp fragments purified. These fragments were then re-cloned into the HindIII-HincII cut preparation of pvHAΔH from above. The portions of the FMDV immunogenic site which have been inserted into HA site A are shown in FIG. 4.

The modified HAΔ (pvHA-80/81, pvHA-82/83, pvHA-122/124) were introduced into the VV genome by homologous recombination using flanking TK sequences, and plaque-picked TK⁻ virus analysed. Viruses were initially screened for their ability to react with polyclonal anti-HA serum in black plaque assays of methanol—and glutataldehyde—fixed plaques. All three modified HAs were able to react with the polyclonal antiserum, and were expressed on the surface of infected cells. The recombinant VVs were then tested for their ability to react with anti-$VP1_{141-160}$ antiserum using glutataldehyde-fixed plaques. Again, all three modified HAs were positive with the anti-peptide serum, while the unmodified recombinant (vHAX31-J34c) was not.

The protein species synthesized in CV-1 cells infected with vHAX31(J34c), vHA80/81(Q3/1), vHA82/83(S6/1) and vHA122/124(T3/1) were examined. Infected cells were labelled with $^{35}S$ methionine and cytoplasmic extracts prepared. The extracts were immune-precipitated using polyclonal anti-HA serum and protein A, and the precipitates examined by SDS-PAGE (Laemmli, 1970). In all cases, a protein species corresponding to $HA_0$ (uncleaved HA) was observed. The species was the same size in all cases, but occasionally a slightly higher mol. wt. band was observed; this may be due to inefficient removal of the signal peptide caused by the extra "junk" amino acids. In some experiments, where a long labelling period was used, there was some processing of $HA_0$ into HA1 and HA2, which co-migrated with those species extracted form purified X31 virus particles.

REFERENCES

Bertholet et al (1985) PNAS 82 2096

Gething and Sambrook (1982) Nature 300 598–625

Laemmli (1970) Nature 227 680–685

Mackett et al (1985a) DNA Cloning, A Practical Approach (ed. D. M. Glover) 2 191 IRL Press Oxford Mackett et al (1985b) Techniques—in Gene Cloning Vol. 2

Messing and Vieira (1982) Gene 19 269–276

Morein et al (1984) Nature 308 457–460

Newton et al (1986) Vaccines 86: New Approaches to Immunization, Cold Spring Harbor Laboratory, 303–309

Smith et al (1983) PNAS 80 7155–59

Verholyen et al (1980) Nature 286 771–776

Wiley et al (1981) Nature 289 373–378

Wilson et al (1981) Nature 289 366–373

We claim:

1. A fusion protein which comprises influenza virus haemagglutinin (HA) and, at antigenic site A of HA, a heterologous epitope, wherein all or part of said antigenic site is replaced by said epitope and said protein presents said epitope in a manner recognizable by an immune system.

2. The protein according to claim 1, wherein said epitope is selected from the group consisting of an epitope of a virus, an epitope of a bacterium and an epitope of a protozoan.

3. The protein according to claim 2, wherein said epitope is selected from the group consisting of an epitope of foot-and-mouth disease virus, an epitope of poliovirus, an epitope of human rhinovirus and an epitope of hepatitis B virus.

4. The protein according to claim 2, wherein said epitope is an epitope of *Plasmodium falciparum*.

* * * * *